US00PP16134P2

(12) United States Plant Patent
Smith

(10) Patent No.: US PP16,134 P2
(45) Date of Patent: Nov. 29, 2005

(54) *CHRYSANTHEMUM* PLANT NAMED 'YOBRANDI'

(50) Latin Name: *Chrysanthemum×morifolium*
Varietal Denomination: Yobrandi

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 38 days.

(21) Appl. No.: 10/937,782

(22) Filed: Sep. 8, 2004

(51) Int. Cl.[7] ..... A01H 5/00
(52) U.S. Cl. ..... Plt./293
(58) Field of Search ..... Plt./293

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yobrandi', characterized by its upright, outwardly spreading and rounded plant habit; freely branching habit; freely flowering habit; decorative-type inflorescences with elongated oblong-shaped ray florets; dark red-colored ray florets; natural season flowering in late September in the Northern Hemisphere; and good garden performance.

2 Drawing Sheets

Botanical classification/cultivar designation: *Chrysanthemum×morifolium* cultivar Yobrandi.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yobrandi'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret coloration and good garden performance.

The new *Chrysanthemum* originated from a cross-pollination made in November, 1999 in Salinas, Calif., of a proprietary *Chrysanthemum×morifolium* seedling selection identified as code number 93- L355001, not patented, as the female, or seed, parent with a proprietary *Chrysanthemum×morifolium* seedling selection identified as code number 96-L011, not patented, as the male, or pollen, parent. The new *Chrysanthemum* was discovered and selected by the Inventor as a single flowering plant within the progeny of the stated cross-pollination grown in a controlled environment in Alva, Fla. in October, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Yobrandi has not been observed under all possible environmental conditions. The phenotype may vary somewhat with variations in environment such as temperature, daylength and light intensity, without, however, any variance in genotype.

The following traits have been repeatedly observed and are determined to be unique characteristics of 'Yobrandi'. These characteristics in combination distinguish 'Yobrandi' as a new and distinct cultivar of *Chrysanthemum:*

1. Upright, outwardly spreading and rounded plant habit.
2. Freely branching habit.
3. Freely flowering habit.
4. Decorative-type inflorescences with elongated oblong-shaped ray florets.
5. Dark red-colored ray florets.
6. Natural season flowering in late September in the Northern Hemisphere.
7. Good garden performance.

In side-by-side comparisons conducted in Alva, Fla. under natural season conditions, plants of the new *Chrysanthemum* differed from plants of the female parent, the proprietary seedling selection identified as code number 93-L355001, in the following characteristics:

1. Plants of the new *Chrysanthemum* had smaller inflorescences than plants of the female parent selection.
2. Plants of the new *Chrysanthemum* and the female parent selection differed in ray floret coloration as plants of the female parent selection had coral-colored ray florets.

In side-by-side comparisons conducted in Alva, Fla. under natural season conditions, plants of the new *Chrysanthemum* differed from plants of the male parent, the proprietary seedling selection identified as code number 96-L011, in the following characteristics:

1. Plants of the new *Chrysanthemum* flowered more uniformly than plants of the male parent selection.
2. Plants of the new *Chrysanthemum* had darker red-colored ray florets than plants of the male parent selection.

Plants of the new *Chrysanthemum* can be compared to plants of the *Chrysanthemum* cultivar Helen, disclosed in U.S. Plant Pat. No. 9,793. In side-by-side comparisons conducted in Alva, Fla. under natural season conditions, plants of the new *Chrysanthemum* differed from plants of the cultivar Helen in the following characteristics:

1. Plants of the new *Chrysanthemum* were shorter, more mounded and stronger than plants of the cultivar Helen.
2. Plants of the new *Chrysanthemum* flowered about ten days later than plants of the cultivar Helen.
3. Ray florets of plants of the new *Chrysanthemum* resisted fading better than ray florets of plants of the cultivar Helen.

Plants of the new *Chrysanthemum* can also be compared to plants of the *Chrysanthemum* cultivar Arezzo, not patented. In side-by-side comparisons conducted in Alva, Fla. under natural season conditions, plants of the new *Chrysanthemum* differed from plants of the cultivar Arezzo in the following characteristics:

1. Plants of the new *Chrysanthemum* were more mounded and more outwardly spreading than plants of the cultivar Arezzo.
2. Ray florets of plants of the new *Chrysanthemum* were darker red in color and resisted fading better than ray florets of plants of the cultivar Arezzo.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yobrandi' grown in a container.

The photograph on the second sheet comprises a close-up view of typical inflorescences of the cultivar 'Yobrandi'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yobrandi.

Commercial classification: Decorative-type garden *Chrysanthemum*.

Parentage:

*Female, or seed, parent.*—Proprietary *Chrysanthemum×morifolium* seedling selection identified as code number 93-L355001, not patented.

*Male, or pollen, parent.*—Proprietary *Chrysanthemum×morifolium* seedling selection identified as code number 96-L001, not patented.

Propagation:

*Type.*—Terminal vegatative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with rounded crown. Stems initially upright, then outwardly spreading. Freely branching with about ten lateral branches per plant. Moderately vigorous.

*Plant height.*—About 16.5 cm.

*Plant diameter.*—About 29 cm.

*Lateral branches.*—Length: About 15 cm. Diameter: About 5 mm. Internode length: About 1 cm. Strength: Strong. Texture: Pubescent. Color: Darker than 146A overlain with close to 187A.

*Foliage description.*—Leaf arrangement: Alternate. Length: About 4.1 cm. Width: About 3.7 cm. Apex: Mucronate. Base: Truncate. Margin: Palmately and deeply lobed; sinuses mostly divergent. Texture, upper and lower surfaces: Pubescent. Color: Developing foliage, upper surface: Darker green than 147A. Developing foliage, lower surface: Close to 147A. Fully expanded foliage, upper surface: More green than 147A. Fully expanded foliage, lower surface: More green than 147B. Venation, upper surface: More green than 147A. Venation, lower surface: More green than 147B. Petiole: Length: About 2.1 cm. Diameter: About 4 mm. Texture, upper and lower surfaces: Pubescent. Color, upper and lower surfaces: Close to 146A.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherically in shape. Freely flowering habit; about 13 inflorescences develop per lateral branch. Inflorescences persistent. Inflorescences not fragrant.

*Flowering response.*—Under natural season conditions, plants flower in late September in the Northern Hemisphere.

*Inflorescence bud (before showing color).*—Height: About 8 mm. Diameter: About 1 cm. Shape: Oblate: Color (lower surface of phyllaries): Darker green than 144A.

*Inflorescence size.*—Diameter: About 4.75 cm. Depth (height): About 2.5 cm. Disc diameter: About 4 mm. Receptacle diameter: About 5 mm. Receptacle height: About 4 mm.

*Ray florets.*—Shape: Elongated oblong. Length: About 2.7 cm. Corolla tube length: About 5 mm. Width: About 8 mm. Apex: Emarginate. Margin: Fused. Texture: Smooth, glabrous; satiny. Surface: Concave. Orientation: Initially upright, then perpendicular to the peduncle. Number of ray florets per inflorescence: About 198 in numerous whorls. Color: When opening, upper and lower surfaces: Between 59A and 187A. Fully opened, upper surface: Close to 10B overlain with cose to 187A to 187B to 59A. Fully opened, lower surface: Close to 144C underlain with close to 187A to 59A.

*Disc florets.*—Shape: Tubular; apex dentate, five-pointed. Length: About 5.5 mm. Width, apex: About 2 mm. Width, base: About 1 mm. Number of disc florets per inflorescence: Very few, less than 15; inconspicuous. Color: Immature: Close to 154A. Mature: Apex: Close to 9A. Mid-section: Close to 154D. Base: More green than 155D.

*Phyllaries*: Quantity per inflorescence: About 18. Length: About 7 mm. Width: About 5 mm. Shape: Deltoid, elongated. Apex: Acute. Base: Truncate, fused. Margin: Entire. Texture, upper surface: Smooth, waxy. Texture, lower surface: Pubescent. Color, upper surface: Close to 146A. Color, lower surface: Darker green than 144A to close to 147A.

*Peduncle.*—Length: First peduncle: About 5.75 cm. Fourth peduncle: About 6.8 cm. Seventh peduncle: About 8.4 cm. Diameter: About 3 mm. Strength: Strong. Aspect: About 40 to 45° from vertical. Texture: Pubescent. Color: Darker green than 146A faintly overlain with close to 187A.

*Reproductive organs.*—Androecium: Present on disc florets only. Anther color: 12A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Yobrandi', as illustrated and described.

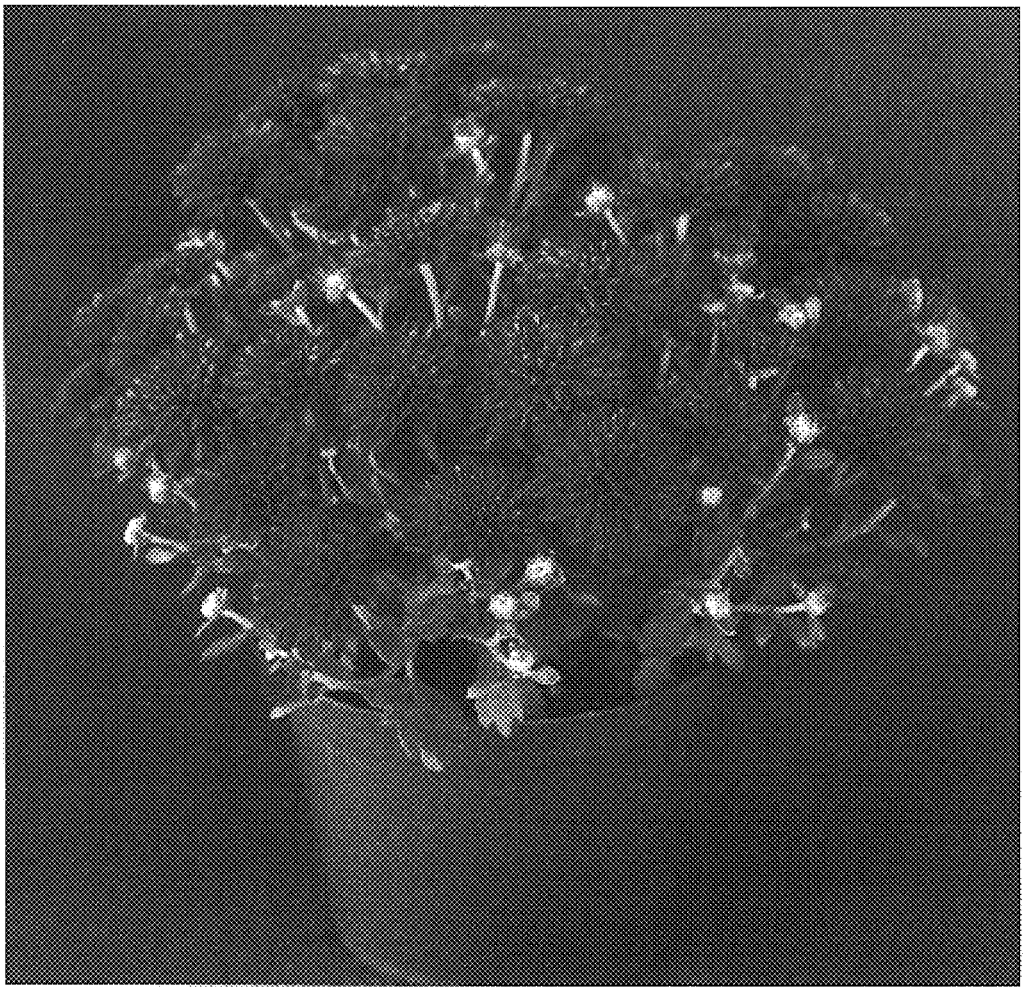

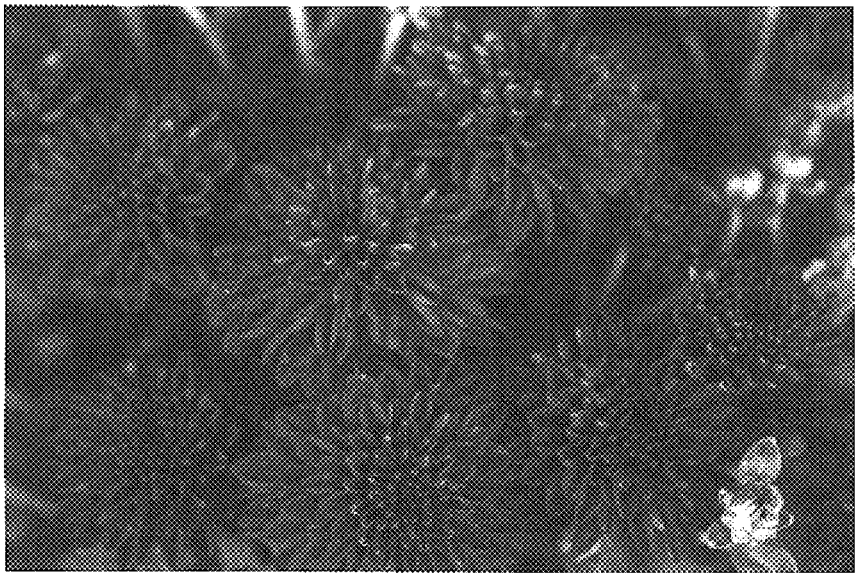

* * * * *